United States Patent [19]

Ogawa et al.

[11] Patent Number: 5,420,243
[45] Date of Patent: May 30, 1995

[54] BIOLOGICALLY ACTIVE TGF-β2 PEPTIDES

[75] Inventors: Yasushi Ogawa, Pacifica; David Schmidt, Santa Cruz, both of Calif.

[73] Assignee: Celtrix Pharmaceuticals, Inc., Santa Clara, Calif.

[21] Appl. No.: 9,448

[22] Filed: Jan. 26, 1993

[51] Int. Cl.$^6$ .............................................. A61K 38/18
[52] U.S. Cl. .................... 530/324; 530/399; 930/120
[58] Field of Search ............. 530/399, 326, 324, 325; 514/12, 13; 930/120

[56] References Cited

U.S. PATENT DOCUMENTS 4,806,523 2/1989 Bentz et al. ............................ 514/2
4,822,606 4/1989 Snyderman et al. ................. 424/88
5,061,786 10/1991 Burnier et al. ....................... 530/326

FOREIGN PATENT DOCUMENTS 0353722 2/1990 European Pat. Off. .
WO90/14359 11/1990 WIPO .

OTHER PUBLICATIONS

Tam et al *Int J Peptide Protein Res* 39:464–71 (1992).
Cianciolo et al *Clinical Research* 38(2):325A (1990).
Van den Eijnden–VanRaaij et al. *J. of Immunol Methods* 133:107–118 (1990).
Hazarika et al *Life Science* 42:252831 (1988).

*Primary Examiner*—Garnette D. Draper
*Assistant Examiner*—Shelly Guest Cermak
*Attorney, Agent, or Firm*—Morrison & Foerster

[57] ABSTRACT

The invention relates to peptides corresponding to regions of the amino acid sequence of TGF-β1 or TGF-β2 which retain, either in monomeric or polymeric forms, at least some of the biological activity of the respective full length TGF-β. The monomeric form of the peptide derived from TGF-β1 comprises the following amino acid sequence: CVRQLYIDFRKDLGWKWIHEPKGYHANFCLGP (SEQ ID NO: 1). The monomeric form of the peptide derived from TGF-β2 comprises the following amino acid sequence: CLRPLYIDFKRDLGWKWIHEPKGYNANFCAGA (SEQ ID NO: 2). Dimers may be formed via disulfide bonds between the amino-terminal cysteine residues, the carboxy-terminal cysteine residues, or amino- and carboxy-terminal cysteine residues of the monomer subunits.

11 Claims, 8 Drawing Sheets

BIOLOGICALLY ACTIVE TGF-β2 PEPTIDES

TECHNICAL FIELD

The present invention relates to biologically active, peptides corresponding to regions of the amino acid sequence of transforming growth factor β1 or β2 that are capable of mimicking the activity of the respective full length TGF-βs.

BACKGROUND OF THE INVENTION

PCT WO 84/001106, filed Sep. 23, 1983, describes transforming growth factor β1 (TGF-β1) and its use for the promotion of cell proliferation and tissue repair, wound healing and treatment of trauma.

U.S. Pat. No. 4,843,063 describes two cartilage inducing factors, CIF-A and CIF-B, found in mammalian bone that (1) are cofactors for inducing cartilage formation in vivo; (2) promote connective tissue deposition in vivo in the absence of any added activating agent or cofactor; and (3) are active in the anchorage-independent cell growth assay used to characterize TGF-β. The assay is referred to as the TGF-β assay herein and is described in *Methods for Preparation of Media, Supplements, and Substrate for Serum-free Animal Cell Culture* (1984) pp. 181–194, Alan R. Liss, Inc.

U.S. Pat. No. 4,806,523, filed Mar. 6, 1986, discloses that CIF-A and CIF-B both possess anti-inflammatory activity and are inhibitors of mitogen stimulated T cell proliferation and B cell activation. It also reports that CIF is localized in centers of hematopoiesis and lymphopoiesis and that CIF may, therefore, be useful for treating indications associated with malfunction or dysfunction of hematopoiesis or lymphopoiesis. CIF-A has since been shown to be identical to TGF-β1. CIF-B has since been recognized as a new form of β-type transforming growth factor and is now called TGF-β2.

U.S. Pat. No. 4,822,606, filed Apr. 7, 1986, describes novel peptides having immunosuppressive or immunoregulatory activity. These peptides are based on a 26 amino acid sequence which is highly conserved among retroviruses associated with immunosuppression.

European Patent Application 0 353 772 A2, filed Aug. 4, 1988, discloses a method and compositions for inhibiting proliferation of epidermal cells with TGF-β1, TGF-β2, or a fragment thereof.

U.S. Pat. No. 5,061,786, filed May 25, 1989, discloses a biologically active peptide corresponding to residues 16–31 of TGF-β1, with optional extensions of the amino terminus.

DISCLOSURE OF THE INVENTION

The invention relates to biologically active peptides corresponding to regions of the amino acid sequence of TGF-β1 or of TGF-β2. The peptides retain and thus mimic the biological activities of mature, active TGF-βs. The peptides are thus suitable for use in any application for which TGF-βs are indicated. The peptides, either in monomeric or polymeric forms, retain at least some of the biological activity of the respective full length TGF-β. The monomeric form of the peptide derived from TGF-β1 comprises the following amino acid sequence: CVRQLYIDFRKDLGWKWIHEPKGYHANFCLGP (SEQ ID No: 1). The monomeric form of the peptide derived from TGF-β2 comprises the following amino acid sequence: CLRPLYIDFKRDLGWKWIHEPKGYNANFCAGA (SEQ ID NO: 2). Dimers may be formed via disulfide bonds between the amino-terminal, carboxy-terminal, or amino- and carboxy-terminal cysteine residues of the monomer subunits.

The present invention further provides compositions comprising the peptides of the invention and a pharmaceutically acceptable carrier therefor and methods of mimicking the effects of TGF-βs comprising administering to a patient an effective amount of such a composition.

These and other embodiments of the present invention will be readily apparent to those of ordinary skill in view of the disclosure herein.

BRIEF DESCRIPTION OF THE DRAWING

FIG. 1a shows the inhibition curves (absorbance vs. concentration) for a TGF-$\beta 1_{16\text{-}31}$ dimer and TGF-β2.

FIG. 1b shows the inhibition curves (absorbance vs. concentration) for a TGF-$\beta 1_{16\text{-}47}$ monomer and TGF-β2.

FIG. 1c shows the inhibition curves (absorbance vs. concentration) for a TGF-$\beta 1_{16\text{-}47}$, fraction 8 (F8), dimer and TGF-β2.

FIG. 1d shows the inhibition curves (absorbance vs. concentration) for a TGF-$\beta 2_{16\text{-}47}$ dimer and TGF-β2.

FIG. 1e shows the inhibition curves (absorbance vs. concentration) for a TGF-$\beta 2_{16\text{-}31}$ dimer and TGF-β2.

FIG. 1f shows the inhibition curves (absorbance vs. concentration) for a TGF-$\beta 1_{16\text{-}47}$, fraction 7 (F7), dimer and TGF-β2.

FIG. 1g shows the inhibition curves (absorbance vs. concentration) for a TGF-$\beta 1_{16\text{-}47}$ trimer and TGF-β2.

FIG. 1h shows the inhibition curves (absorbance vs. concentration) for the control (bovine serum albumin) and TGF-β2.

DETAILED DESCRIPTION

Figure 1A:
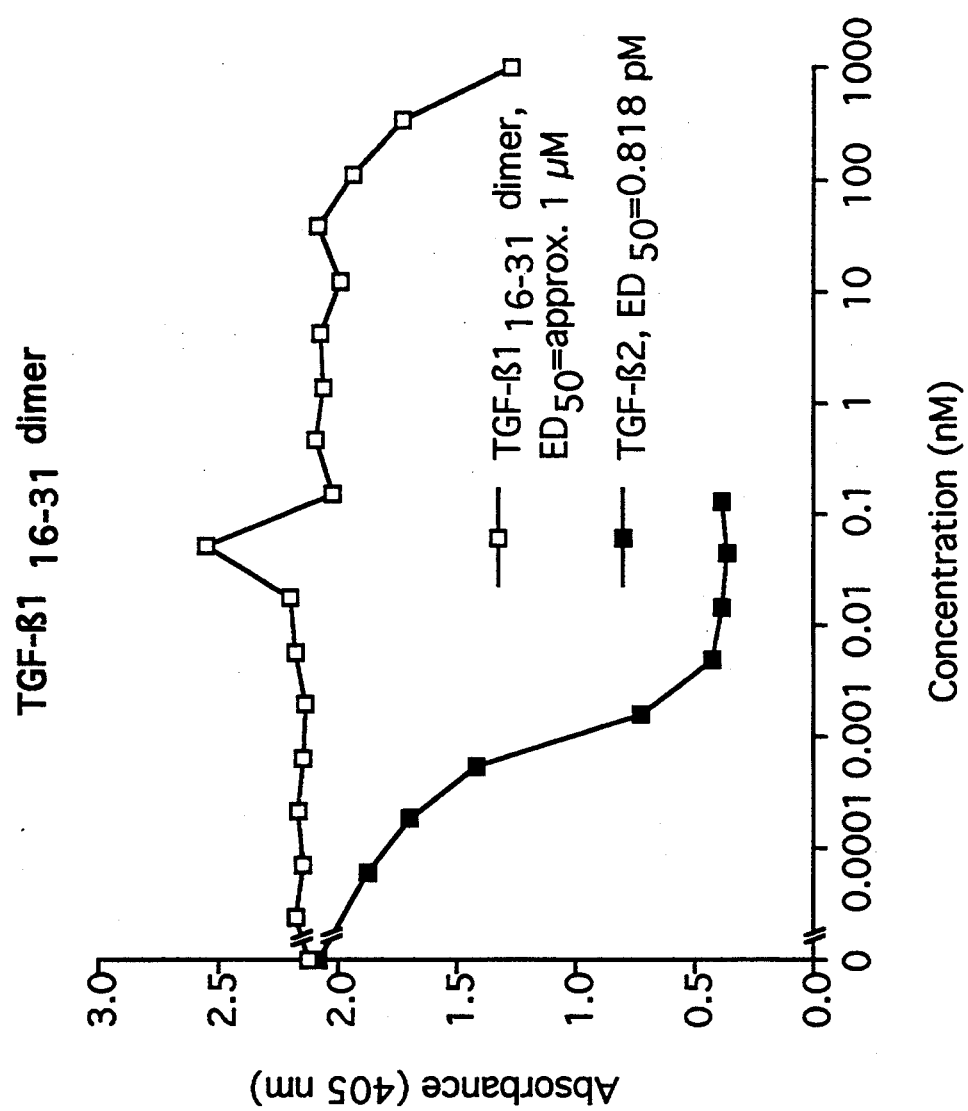
FIGS. 1a through 1h depict the results of the mink lung cell proliferation assay described in Example 2. More particularly.

Technical and scientific terms have been defined herein and this disclosure and the appended claims should be interpreted in view of those definitions. Unless specifically defined herein, all other technical and scientific terms have the same meaning as commonly understood by one of ordinary skill in the art to which this invention pertains. Although other methods and materials similar or equivalent to those described may be used in the practice or testing of the present invention, the preferred methods and materials are described herein.

It must be noted that as used in this specification and the appended claims, the singular forms "a", "an" and "the" include plural references unless the context clearly dictates otherwise. Thus, for example, reference to "a peptide" or "an active peptide" includes mixtures of peptides of the general type described herein, and reference to "the method of administration" includes one or more methods of administration of the general type described herein and/or of the type which will be readily apparent to those of ordinary skill in the art.

The methods for making the peptides employ, unless otherwise indicated, conventional techniques of synthetic organic chemistry, protein chemistry, molecular biology, microbiology, and recombinant DNA technology, which are within the skill of one in the art. Such techniques are explained fully in the literature. See, e.g., Scopes, *Protein Purification Principles and Practices,* 2d ed. (Springer-Verlag, 1987), *Methods in Enzymology* (Colowick and Kaplan, eds., Academic Press, Inc.); Sambrook et al., *Molecular Cloning: A Laboratory Manual,* 2d ed., Cold Spring Harbor Press, Cold Spring Harbor, NY, 1989, *Handbook of Experimental Immunology,* Vols. I-IV, (Weir and Blackwell, eds) (Blackwell Scientific Publications, 1986); House, *Modern Synthetic Reactions,* 2nd ed., Benjamin/Cummings, Menlo Park, Calif., 1972. Atherton and Sheppard, *Solid Phase Peptide Synthesis: A Practical Approach* (Oxford University Press, 1989); Steward and Young *Solid Phase Peptide Synthesis,* 2nd ed. (Pierce Chemical Co., 1984).

All patents, patent applications, and publications mentioned herein, whether supra or infra, are hereby incorporated by reference in their entirety.

A. Definitions

In defining the present invention, the following terms will be employed, and are intended to be defined as indicated below.

As used herein, the amino acid sequence of TGF-$\beta$1 is that described by Derynck et al., Nucl. Acids Res., 15:3188-3189 (1987). The amino acid sequence of TGF-$\beta$2 is that described by Madisen et al., DNA, 7:1-8 (1988).

As used herein, the term "fibrinogenic" refers to factors that promote healing of damaged connective tissue resulting from injury inflicted by various types of trauma, inflammation, and immune reactions. These factors include but are not limited to those involved in fibroblast chemotaxis, synthesis of collagen, hyaluronate, and tissue inhibitor of metalloproteinase (TIMP).

As used herein, the phrase "biologically active" refers to the ability to mediate a biological function.

As used herein, the term "peptide" refers to an oligomer of at least two contiguous amino acid residues. Further, as used herein, the phrase "the peptides" refers to the peptides described herein unless otherwise indicated.

As used herein, the term "treat" is intended to mean prophylaxis or attenuation of an existing condition. Accordingly, in the case of inflammation, the invention method may be used to prevent inflammation or alleviate existing inflammation.

As used herein, the term "inflammation" is intended to encompass both acute responses (i.e. a response in which the inflammatory processes are active) and chronic responses (i.e. a response marked by slow progress and formation of new connective tissue). Chronic and acute inflammation may be distinguished by the cell types involved. Acute inflammation often involves polymorphonuclear neutrophils; whereas chronic inflammation is normally characterized by a lymphohistiocytic and/or granulomatous response. Examples of specific types of inflammation are diffuse inflammation, focal inflammation, croupous inflammation, interstitial inflammation, obliterative inflammation, reactive inflammation, specific inflammation, toxic inflammation, and traumatic inflammation.

As used herein, an amino acid sequence "substantially corresponding" to TGF-$\beta$1 or TGF-$\beta$2 will have at least 70% sequence homology with the amino acid sequence of TGF-$\beta$1 or TGF-$\beta$2, respectively, and retain functional activity. Further, it is preferable that any differences in sequence homology possessed by a peptide or protein having a "substantially corresponding" sequence are differences which do not adversely affect a desired property of that peptide or protein.

As used herein, the term "septic shock" refers to the sequence of events triggered by bacteremia during which cell wall substances (endotoxin in Gram-negative organisms and peptidoglycan/teichoic acid complex in Gram-positive organisms) activate the complement, kinin, and ACTH/endorphin systems. This series of metabolic events ultimately progresses to a state of shock.

As used herein, the term "patient" refers to animals including humans suffering from a condition that can be cured or ameliorated by a TGF-$\beta$.

B. General Methods

TGF-$\beta$s exhibit activity in the TGF-$\beta$ assay described in *Methods for Preparation of Media, Supplements, and Substrate for Serum-free Animal Cell Culture* (1984) pp. 181-194, Alan R. Liss, Inc. The assay determines the ability to induce anchorage-independent growth in non-neoplastic normal rat kidney fibroblasts by measuring the formation of cell colonies in soft agar.

TGF-$\beta$s isolated to date are nonspecies specific as regards TGF-$\beta$ activity. TGF-$\beta$s derived from other species are thus highly "homologous" in that they are similar in amino acid residue sequences and activity. These polypeptides are believed to have been highly conserved among animal species (i.e, wherein a given polypeptide from different mammalian species has an amino acid sequence that varies little, if at all, between species with respect to amino acid residue deletions, additives, or substitutions, and which variations do not adversely affect the non-species-specific activity of the molecule adversely) and have cross-species functionality. Accordingly, the peptides may be derived from cells or tissue of diverse animal origin or may be obtained by recombinant DNA technology. The peptides thus encompass the amino acid residue sequences of homologous TGF-$\beta$s. Correlatively, peptides from one vertebrate species may be used to treat another vertebrate species. The most common therapeutic uses of the peptides is in the treatment of patients such as humans, domestic animals such as cattle, sheep, and pigs, and sports or pet animals such as dogs, cats, and horses.

The peptides are useful in any application for which a TGF-$\beta$ is indicated. The peptides mimic TGF-$\beta$ activities including but not limited to inducing cartilage/bone formation and for repairing, replacing, or augmenting cartilage/bone tissue in animals including humans. Effective amounts of the peptides will normally be formulated with pharmacologically acceptable fluids or solid carriers. An effective amount of the peptides is an amount sufficient to evoke the biological response required to ameliorate the condition suffered by the patient.

The peptides may also be used in the same manner as other TGF-$\beta$s to promote (provoke and sustain) non-species specific cellular proliferation. Clinical applications of the cellular proliferation activity of these compositions include topical administration, for instance, for burn or wound healing or tissue repair. In such uses an effective amount of the peptides are formulated with pharmacologically acceptable carriers. An effective amount of the peptides is an amount sufficient to induce soft tissue cell proliferation.

Topical dosage forms of the peptides can be formulated for instance as sprays, gels, ointments, or salves. Suitable dosage forms are those that are pharmacologically acceptable and into which an amount of the peptides can be dispersed so as to allow diffusion of an effective amount of the peptides to the treatment site.

The peptides, alone or in combination, may be dispersed into or incorporated into a polymeric substance and coated onto implants. Such implants include, but are not limited to, collagenous soft and hard tissue implants, prostheses, sponges, wound dressings, and sutures. The peptides modulate local inflammatory responses to these foreign bodies and promote attachment of the implants, particularly prostheses. Since such implants are often made from permeable materials peptides incorporated into the implants can diffuse from the implant to exert their properties.

The peptides may also be useful systemically, for instance, for treating bone deficiencies, such as osteoporosis and osteopetrosis. For such treatment the peptides are formulated in therapeutically effective amounts with injectable carriers and administered parenterally to the patient. The dose is typically be in the range of about 0,001 μg/kg to 10 g/kg with a preferred range of about 100 μg/kg to 1 g/kg.

Systemic dosage forms may be formulated for gastrointestinal administration (i.e., liquids, pills, tablets, or suppositories) or for parenteral injection. The determination of dosages used in such applications are within the skill of one in the art and depend on factors such as the nature of the condition being treated, the size of the patient, and responsiveness to the peptides administered, and are therefore determined by the caregiver.

The peptides may be used as oncostats in treating any type of cellular neoplasm, including, without limitation, carcinomas, myelomas, melanomas, and lymphomas. Particularly preferred targets are breast, lung, colon, and ovarian carcinomas. The peptides may be administered locally or systemically, depending on the nature and degree of the neoplasm being treated. For local administration an oncostatically effective amount of the peptides or mixtures formulated thereof are combined with a pharmacologically acceptable carrier and administered as a solid or semisolid implant which may or may not be of a sustained or a controlled release form. The peptides may also be formulated into an injectable for parenteral administration.

Alternatively, the peptides can be delivered to solid tumors in particular, including inoperable tumors, using current catheter technology for localized delivery via the arterial supply to the tumor. In this indication the peptides are mixed with a vasoocclusive agent, such as injectable collagen, which would provide a means to reduce perfusion of the tumor and at the same time provide for the localized delivery of the peptides. Clips may also be used to occlude venous drainage, and thus maintain high doses of the peptides in the tumor mass.

For systemic administration, oncostatically effective amounts of the peptides are formulated with pharmacologically acceptable carriers used for water soluble proteins including but not limited to physiological saline, sugar solutions and the like for injection into circulation. Alternatively, the peptides may be formulated as a sustained release formulation to release the peptides into the circulation over a prolonged time period.

Specific targeting of the factor for tumor cells in systemic applications may be accomplished for instance by conjugation of a peptide to an antibody directed against tumor specific cell surface antigen(s). Enhanced tumor cell cytotoxicity may be accomplished by covalently radiolabeling the fibrinogenic peptide with $^{131}I$, a cytotoxic agent. The peptides are readily iodinated and retain full biological activity. Monoclonal antibody preparations with specificity for particular tumor types, such as breast and ovarian tumors, are well known in the art. Other oncostats or chemotherapeutic drugs may be included in the formulation if desired.

The term "oncostatically effective" is intended to indicate a dose that effects a significant (>50%) inhibition of tumor cell proliferation. In in vitro assays, 50% inhibition is generally observed at TGF-β concentrations of the order of 0.2 ng/ml and saturation is achieved at 10 ng/ml. Inhibition may be monitored in vivo by monitoring the patient's tumor burden. The dose of peptide that is oncostatically effective in a given treatment depend upon the patient, the type and degree of cancer being treated and the mode of administration. In general, the amounts administered to adult humans are in the range of about 0.001 μg/kg to 10 g/kg. Corresponding systemic administration involves the higher segment of the range (100 μg/kg to 1 g/kg) due to clearance or other in situ inactivation of the polypeptide.

The peptides are useful in the treatment of both local and systemic inflammation. When used as a local antiinflammatory agent, the peptides are usually formulated in effective amounts with pharmacologically acceptable carriers in weight ratios to carrier in the range of 1:1,000 to 1:20,000.

When used to treat inflammation at internal sites locally, the peptides, alone or in combination, may be injected, inhaled, placed surgically, or otherwise administered locally, depending on the particular formulation and the site where inflammation control is desired.

For systemic administration, the peptides may be formulated with conventional carriers used with water soluble proteins for injection into circulation. Alternatively, they may be formulated as a sustained release implant formulation if the indication being treated so requires.

Examples of formulations for systemic, topical, or parental administration may be found in *Remington's Pharmaceutical Sciences*, Gernnaro, ed., Mack Publishing Co., Easton, Pa., 1985, hereby incorporated by reference in its entirety.

The amount of the peptides administered to treat inflammation depends upon the patient, the inflammatory condition being treated, and the mode of administration. In general, amounts administered to adult humans are in the range of about 1 mg to 10 g. When the peptides are administered locally, amounts in the lower portion of the range are normally used, typically 1 μg to 100 mg. Correspondingly, systemic administration typically involves amounts in the 100 μg/kg to 1 g/kg range.

The peptides may be particularly effective in the treatment of inflammation involving the respiratory system. In this application, the peptides may be administered by inhalation with a suitable aerosol. In this form, the peptides would be useful for the treatment of diffuse interstitial diseases of the lung including but not limited to, asbestosis, silicosis, or coal-miner's pneumoconiosis; the treatment of immunological diseases that involve the respiratory tract including, but not limited to, rheumatoid arthritis, lupus erythematosus, or Goodpasture's syndrome; and the treatment of granulomatosis and eosinophilic granulomatosis.

The peptides may be combined with carriers in the form of a salve, ointment, or other topical formulation and thereby be useful in the control of dermal inflammation by topical application. Such formulations would be particularly useful in the local treatment of skin conditions including, but not limited to, psoriasis vulgaris, contact dermatitis, dermal ulcers, and acute or chronic eczematous dermatitis.

The peptides may be used either alone or combined with a slow release carrier and injected into or around joints, bone, or muscle for wound healing or control of inflammation associated with various diseases. Such diseases include but are not limited to myositis (due to viral, bacterial, parasitic, fungal, or autoimmune processes); myasthenia gravis; osteomyelitis; osteoarthritis and rheumatoid arthritis.

Since TGF-$\beta$ molecules have been shown to be stable at low pH and resistant to enzyme digestion, these factors may be delivered gastrointestinally. The peptides are thus particularly useful for the treatment of gastrointestinal disorders including but not limited to gastric and duodenal ulcers, granulomatous gastritis, esophagitis, enteritis and colitis.

TGF-$\beta$s have also been shown to be effective for the treatment of septic shock. International Publication Number WO 90/000903, filed Jul. 21, 1989. The peptides may be administered prophylactically or therapeutically, i.e., before, simultaneous with, or after an infection has set in. The peptides may be used to treat patients who are at-risk to bacterial infection, or who suffer from septicemia. Patients who are at risk include but are not limited to those receiving immunosuppressive therapy and those suffering from severe thermal burns or other serious injury, cystic fibrosis, renal failure, or cancer, or who are undergoing extensive surgical procedures or organ transplantation.

The peptides may further be used to treat a patient for an indication associated with a dysfunction or malfunction of hematopoiesis or lymphopoiesis. The peptides may be administered to these patients by any suitable technique, including systemic or local, as discussed above and will take into consideration the requirements of the individual patient, the method of administration, and other factors known to practitioners. Doses will typically be in the range of from about 100 $\mu$g/kg to 1 g/kg.

The peptides may also be used to protect hematopoietic stem cells from the myelotoxicity of chemotherapeutic drugs, such as cyclophosphamide and mephalan, or radiation therapy. In such applications a therapeutically effective amount of the peptides will be administered usually 3-72 hours prior to the administration of the chemotherapeutic drug or radiation therapy. The mode of administration is preferably interfemoral arterial, intraperitoneal, or subcutaneous, and is preferably by injection. Compositions and doses may be formulated as discussed for the above applications, taking into consideration the requirements of the individual patient, the nature of the drug or radiation therapy used, the method of administration of the composition, and other factors known to practitioners. Doses will typically be in the range of 100 $\mu$g/kg to 1 g/kg.

TGF-$\beta$ may also be used in the prevention of severe cardiac injury resulting from reperfusion of ischemic myocardium. Lefer et al., Science, 249:61 (1990). The peptides thus may be administered, preferably intravenously or intracardiac, prior to or after the onset of ischemia. Peptide compositions and doses may be formulated as discussed for above applications, taking into consideration the requirements of the individual patient and other factors known to practitioners. Doses will typically be in the range of 100 $\mu$g/kg to 1 g/kg.

The following examples are put forth so as to provide those of ordinary skill in the art with a complete disclosure and description of how to make the peptides, formulate the compositions and use them in connection with the invention and are not intended to limit the scope of the invention.

EXAMPLE 1

Peptide Synthesis

The following peptides were synthesized:

TGF-$\beta 1_{16-31}$ corresponds to TGF-$\beta 1$ residues 16 through 31, and has the amino acid sequence

CVRQLYIDFRKDLGWK (SEQ ID NO: 3).

TGF-$\beta 2_{16-31}$ corresponds to TGF-$\beta 2$ residues 16 through 31, and has the amino acid sequence

CLRPLYIDFKRDLGWK (SEQ ID NO: 4).

TGF-$\beta 1_{16-47}$ corresponds to TGF-$\beta 1$ residues 16 through 47, and has the amino acid sequence

CVRQLYIDFRKDLGWKWIHEPK-
GYHANFCLGP (SEQ ID NO: 1).

TGF-$\beta 2_{16-47}$ corresponds to TGF-$\beta 2$ residues 16 through 47, and has the amino acid sequence

CLRPLYIDFKRDLGWKWIHEPKGYNANF-
CAGA (SEQ ID NO: 2).

Peptides were synthesized on an Applied Biosystems model 431A peptide synthesizer using Fmoc amino acids (Applied Biosystems). Fmoc amino acids were coupled through reactions mediated with N,N-dicyclohexylcarbodiimide (DCC) or [2-(1H-benzotriazol-1-yl)-1,1,3,3-tetramethyluronium hexafluorophosphate] (HBTU) in 1-hydroxybenzotriazole (HOBt). The peptide synthesis protocol was modified to double couple certain residues and to shorten the coupling times of certain residues to minimize premature termination of peptide synthesis by diketopiperazine formation. The peptides were synthesized on 4-hydroxymethylphenoxymethyl copolystyrene-1% divinylbenzene resin (HMP-resin). Reactive sites on the HMP-resin were capped with acetic anhydride following addition of the first residue.

The crude peptide (approximately 250 $\mu$mol) was cleaved from the resin in 11.25 ml of 89% TFA, containing 0.75 g of crystalline phenol, 0.25 ml of ethylene dithiol, 0.5 ml of thioanisole, and water, at room temperature for over 1.5 hr. The resin was removed by filtration through a glass fritted disk and the filtrate was concentrated to 2 ml by using a rotoevaporator at 30° C. Crude peptide was precipitated by adding 50 ml of ice-cold diethyl ether and collected by filtration. The crude peptide was dissolved in 0.1% TFA, 30% acetonitrile and lyophilized. The dry peptide was stored at −20° C.

The dried crude peptide was dissolved in 0.1% TFA, 18% acetonitrile and chromatographed on a C18-reverse phase HPLC column (1×25 cm, Vydac, C18TP510). Peptides were eluted with a linear acetonitrile gradient in 0.1% TFA. The peak containing the desired peptide was identified by N-terminal sequencing and was confirmed by amino acid analysis. Protein concentration was determined with a BCA assay (Pierce, Rockford, Ill.). Reduced forms of cysteine residues were assayed using 5,5,'-dithio-bis-(2-nitrobenzoic acid). Ellman, Arch. Biochem. Biophys., 74:443 (1958).

To dimerize and trimerize, peptides, disulfide bonds were formed as follows. Purified peptide was dissolved at 5 mg/ml in 20% acetonitrile/80% dilute ammonium hydroxide (pH adjusted to 8.5 to 9.5 with 3% ammonium hydroxide). After stirring for 1 to 16 hr, precipitate that formed was dissolved by decreasing the pH to approximately 2 with 10% TFA. The reaction mixture was applied onto a C18-reverse phase HPLC column (1×25 cm, Vydac, C18TP510) and eluted with a linear acetonitrile gradient in 0.1% TFA. The dimeric and trimeric forms of the peptides were identified by the shift in the elution position of the peak relative to the monomeric peptides. Monomeric and dimeric trimeric forms were confirmed by assaying for non-disulfide bonded cysteine residues and by mass spectroscopy.

EXAMPLE 2

Cell Proliferation Inhibition Assay

TGF-$\beta$ is known to inhibit proliferation of mink lung epithelial cells. The mink lung epithelial cell assay was thus used to test the ability of the peptides to mimic the biological activity of TGF-$\beta$.

Mink lung epithelial cells (ATCC, Rockville, Md., Mv1Lu CCL64) were plated at $0.5-1.0 \times 10^6$ cells/plate in 100 mm culture plates and grown in Eagle's minimal essential medium (MEM) supplemented with 50 units/ml penicillin, 50 $\mu$g/ml streptomycin, nonessential amino acids, L-glutamine, and 10% fetal bovine serum (FBS). Cells were passaged while the cell density was subconfluent. Cells were detached with trypsin, collected by centrifugation at 800×g for 2 min, and resuspended in the culture medium at 20,000 cells/mi. The cells were plated in 96-well microtiter plates at 1000 cells (50 $\mu$l)/well.

Peptides TGF-$\beta1_{16-31}$, TGF-$\beta1_{16-47}$, TGF-$\beta2_{16-31}$, TGF-$\beta2_{16-47}$ in monomeric and dimeric forms were lyophilized in the presence of sterile bovine serum albumin (BSA) carrier. A trimeric form of TGF-$\beta1_{16-47}$ was similarly lyophilized. Samples (50 $\mu$l) of the peptides were dissolved in the cell culture medium and added to the wells in triplicate. Recombinant human TGF-$\beta2$ was used as the standard. The plates were incubated under a 5% $CO_2$/95% (V/V) air atmosphere at 37° C. for 4 days.

The number of cells/well in this assay is proportional to the activity of the constitutively expressed enzyme, acid phosphatase. To measure acid phosphatase activity, the wells were rinsed with phosphate-buffered saline (PBS), filled with 100 $\mu$l of 0.1M sodium acetate, pH 5.5/0.1% Triton X-100/100 mM p-nitrophenyl phosphate, and the plates were incubated at 37° C. for 2 hr. Ten $\mu$l of 1.0N NaOH was added to each well, and after 20 min at room temperature, the absorbance at 405 nm was measured.

Figure 1B:
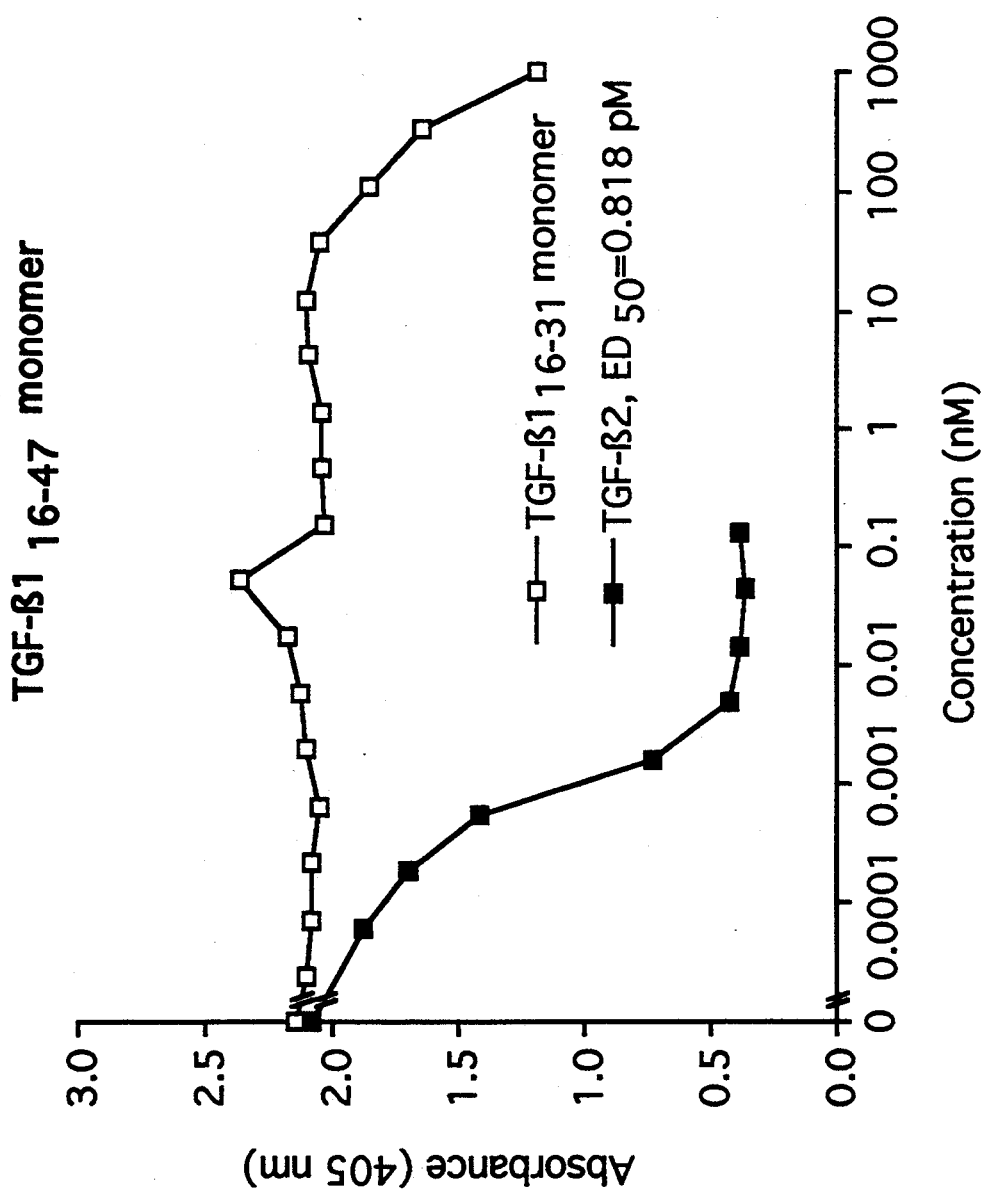
Figure 1C:
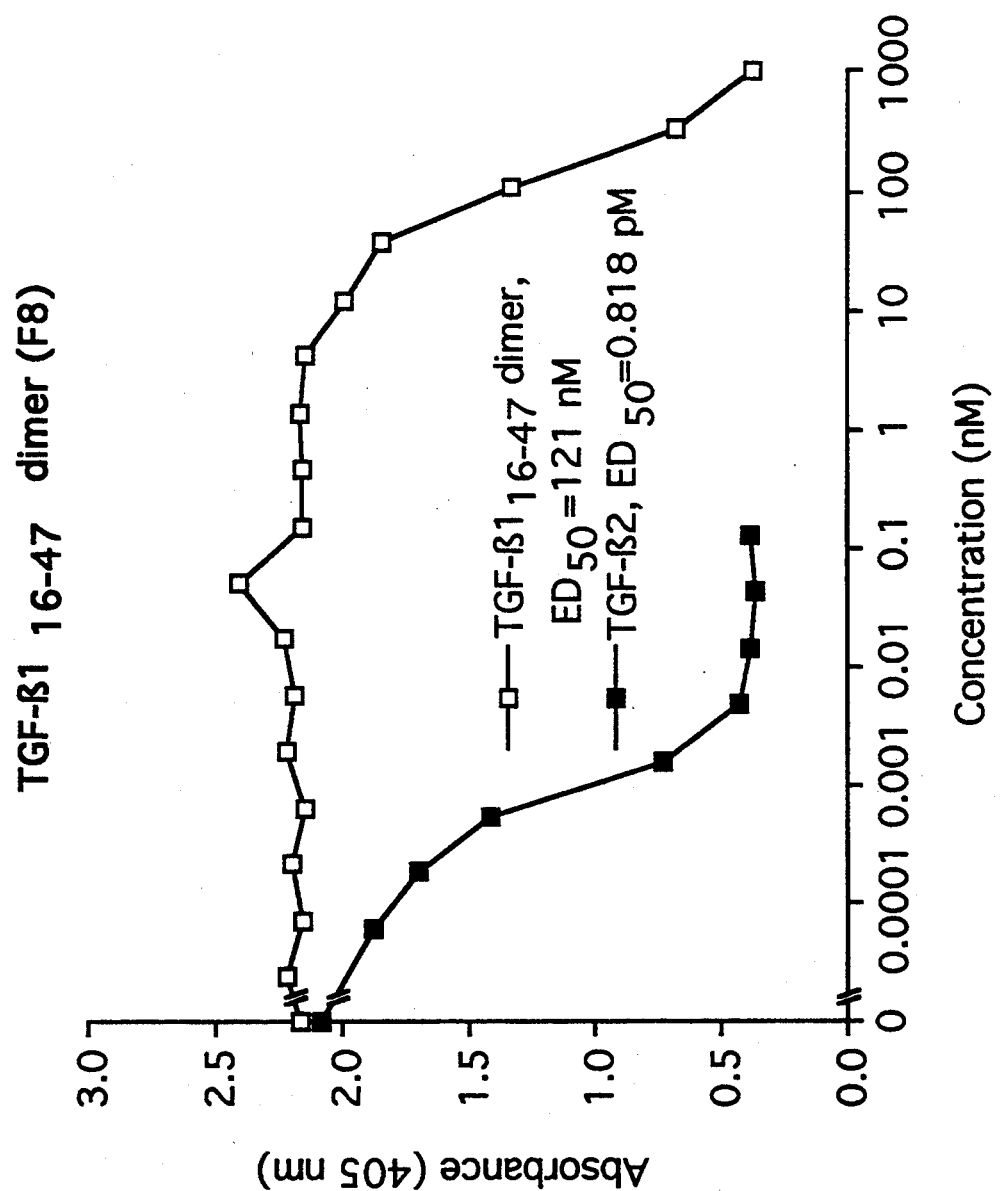
Figure 1D:
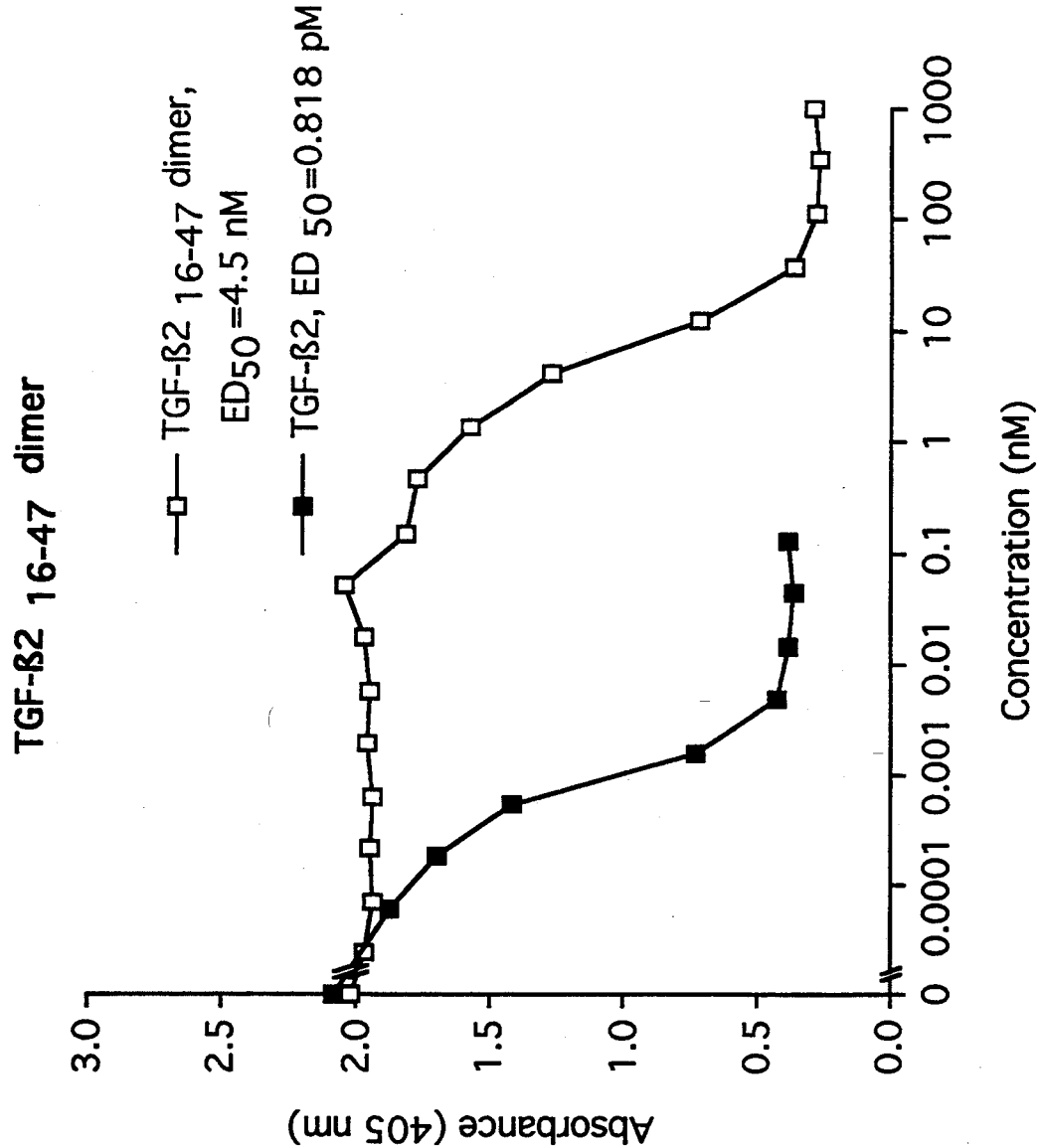
Figure 1E:
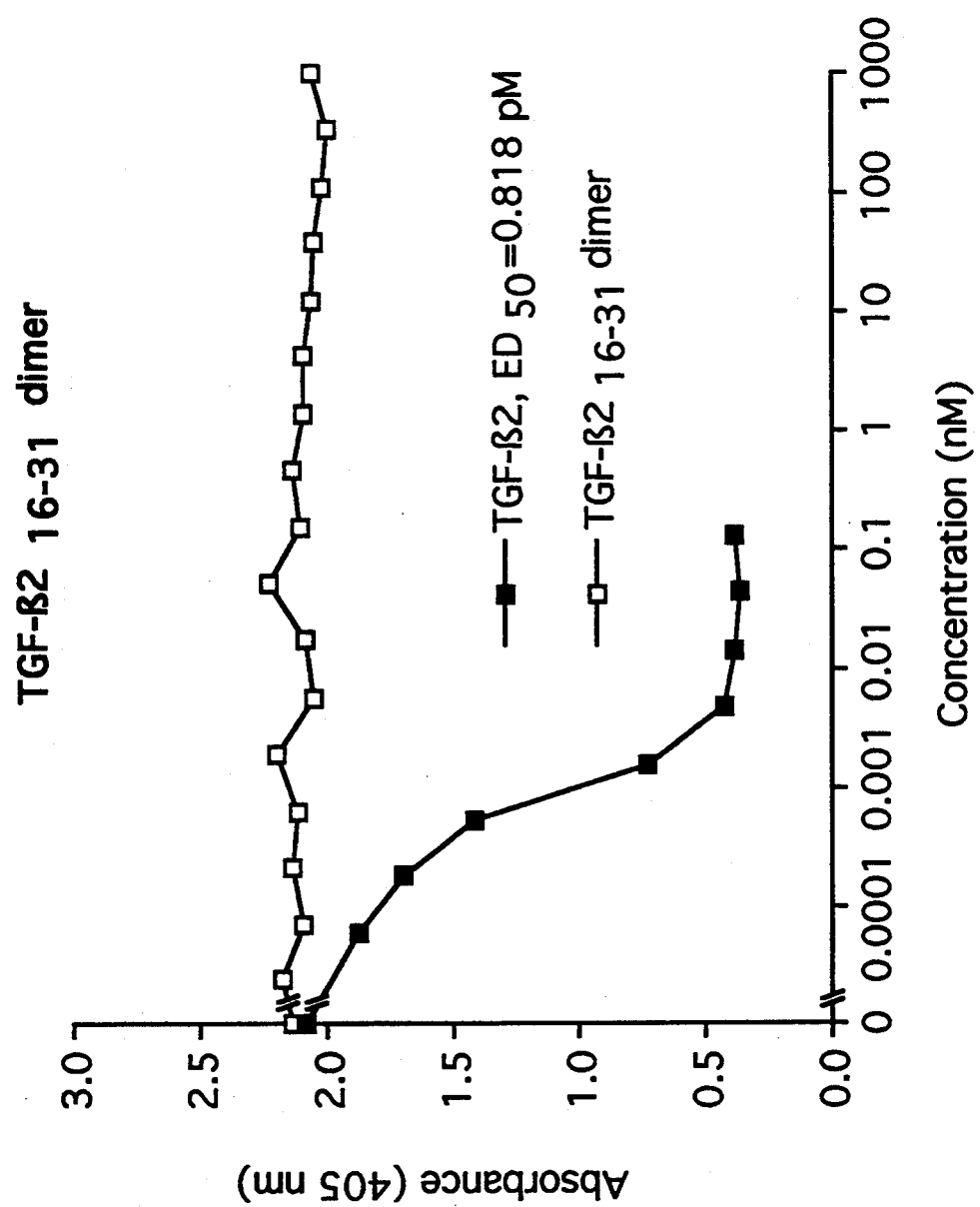
Figure 1F:
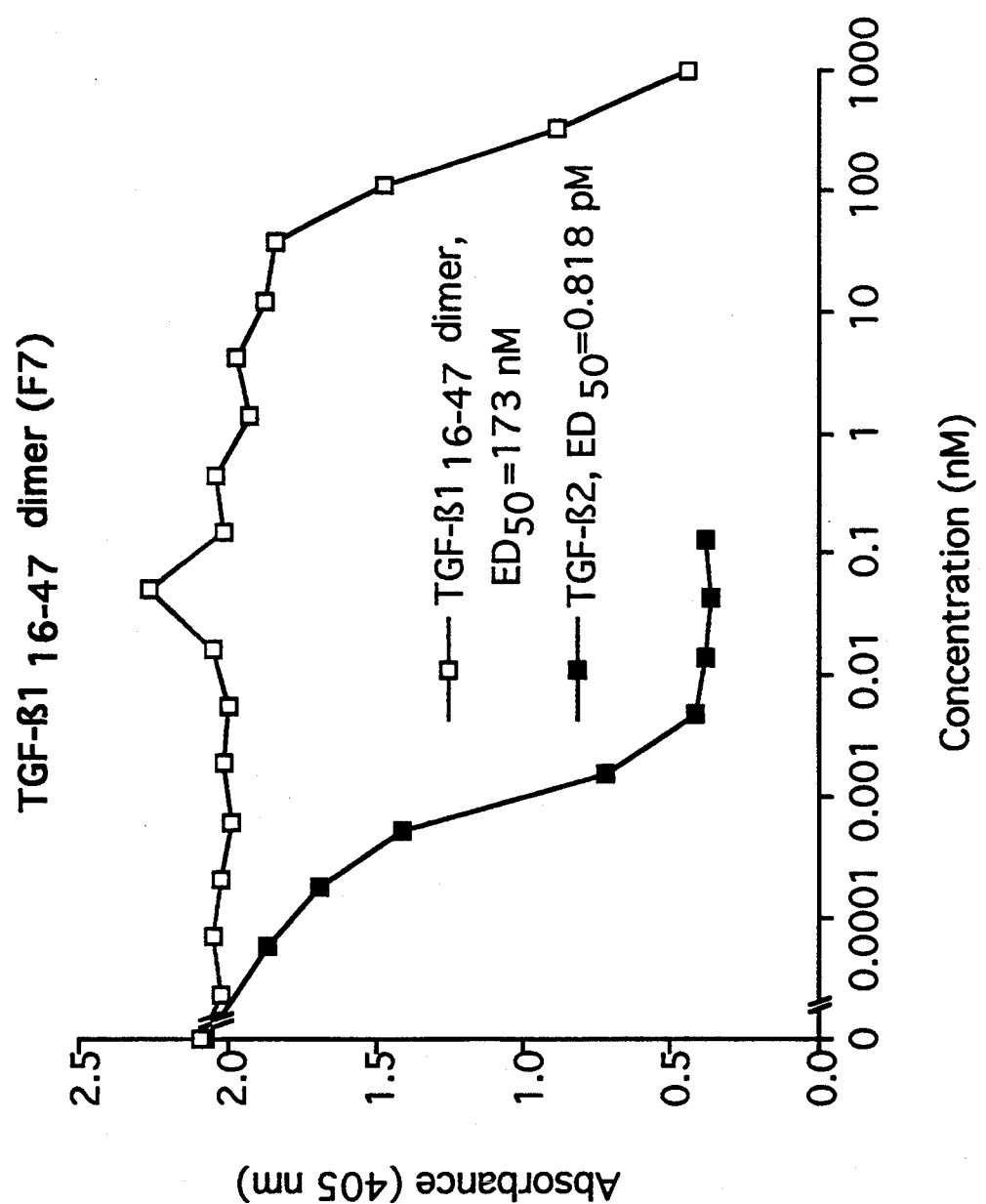
Figure 1G:
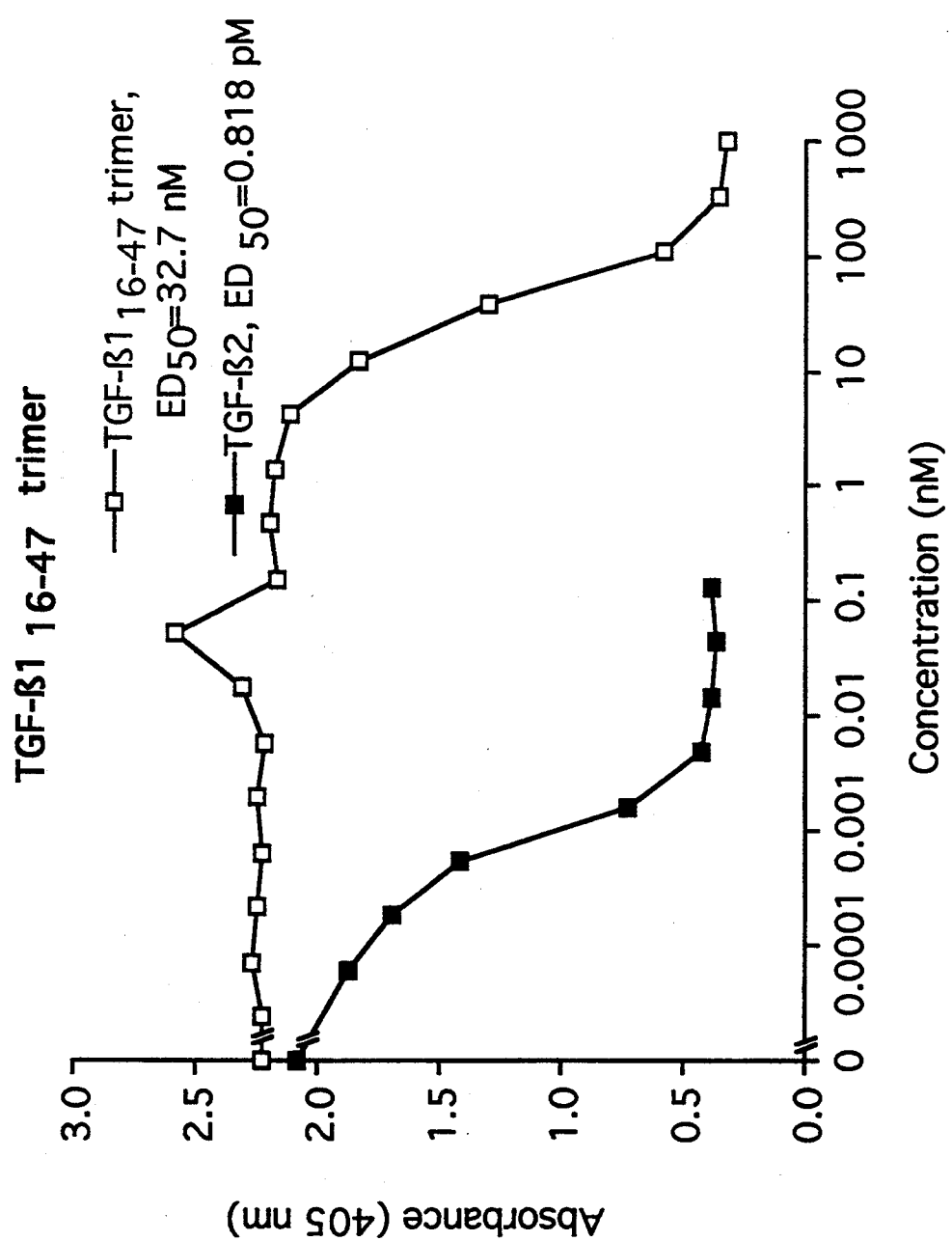
Figure 1H:
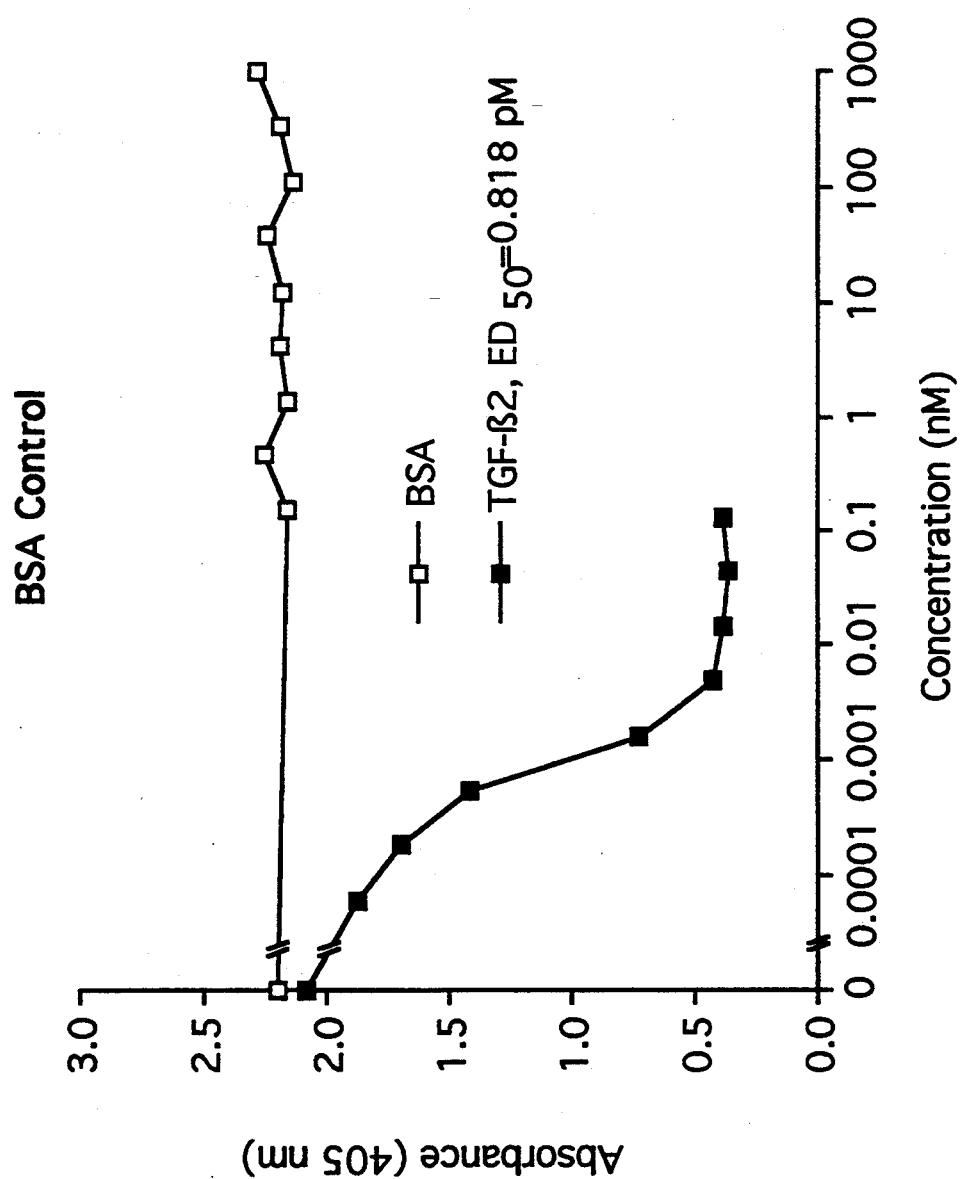

Some of the synthetic peptides and TGF-$\beta2$ inhibited proliferation of the mink lung epithelial cells in a dose-dependant manner (FIG. 1), as indicated by the decrease in absorbance values. The inhibition curve for TGF-$\beta2$ has been included in each figure for comparison. Approximate concentrations at which a given peptide and TGF-$\beta2$ inhibited cell proliferation half-maximally ($ED_{50}$) are summarized in Table 1.

TABLE 1

| Peptide | | $ED_{50}$ |
| --- | --- | --- |
| TGF-$\beta1_{16-31}$ | dimer | 1–3 $\mu$M |
| | monomer | not active |
| TGF-$\beta2_{16-31}$ | dimer | not active |
| | monomer | not active |
| TGF-$\beta1_{16-47}$ | dimer | 150 nM |
| | monomer | 1 $\mu$M |
| | trimer | 32.7 nM |
| TGF-$\beta2_{16-47}$ | dimer | 4–14 nM |
| | monomer | not active |
| TGF-$\beta2$ | | 0.4–1 pM |

TGF-$\beta1_{16-31}$ dimer inhibited proliferation of mink lung epithelial cells with an $ED_{50}$ of 1–3 $\mu$M, comparable to levels of specific biological activity previously reported for this peptide. Chen et al., J. Bone Min. Res., 5: Abstract 26; and WO 90/14359. TGF-$\beta2_{16-31}$ a peptide homologous to the TGF-$\beta1_{16-31}$ peptide, was not active in either monomeric or dimeric form in the assay. The activity of the TGF-$\beta1$ synthetic peptide increased considerably when 16 additional carboxy terminal amino acid residues were added to form TGF-$\beta1_{16-47}$. The dimer of TGF-$\beta1_{16-47}$ exhibited an $ED_{50}$ of about 150 nM. TGF-$\beta1_{16-47}$ peptide monomer exhibited some activity. The trimer of TGF-$\beta1_{16-47}$ exhibited an $Ed_{50}$ of about 32.7 nM. In contrast to all the peptides mentioned, TGF-$\beta2_{16-47}$ peptide dimer exhibited an $ED_{50}$ of about 4–14 nM. In comparison, bovine bone TGF-$\beta2$ inhibited proliferation of the cells with an $ED_{50}$ of 0.4 to 1.0 pM. BSA alone was inactive in this assay. Thus, dimerized TGF-$\beta2_{16-47}$ possesses about 11–38 fold more activity than dimerized TGF-$\beta1_{16-47}$. None of the monomeric peptides were active below 1 $\mu$M.

It should be noted that activities of these peptides when assayed in the cell culture assay without prior lyophilization was comparable to the peptides colyophilized with BSA carrier prior to the assay.

EXAMPLE 3

Inhibition Of Murine Thymocyte Proliferation

In order to determine the effect of the peptides on proliferation of cell types other than mink lung epithelial cells, murine thymocytes were exposed to the peptides. Proliferation was measured by determining the amount of $^3$H-thymidine incorporated into the thymocyte DNA in response to the peptides. The cell culture assay was performed as described by Ellingsworth et al., Cell. Immunol., 114:41–54 (1988). Single-cell suspensions of thymocytes were prepared from 4 to 8 week old C3H/HeJ mice and the cells were suspended in Eagle's MEM supplemented with 5% fetal calf serum (FCS), 100 units/ml penicillin, 100 $\mu$g/ml streptomycin, 2 mM L-glutamine and 50 $\mu$M $\beta$-mercaptoethanol to $6.66 \times 10^6$ cells/ml. The thymocytes were plated into 96-well microtiter plates at $10^6$ cells/well (150 $\mu$l). The cells were activated with 1.0 $\mu$g/ml of phytohemagglutinin and 8 units/ml of interleukin-1 (IL-1) (Boehringer Mannheim, Indianapolis, Ind.). 0.02 to 200 pmol of the peptides or 0.02 to 50 fmol of TGF-$\beta2$ were added and the total volume was adjusted to 250 $\mu$l with the culture medium. The cells were incubated at 37° C. for 72 hr in a humidified incubator in 5% $CO_2$-95% air atmosphere. The cells were pulsed with 0.5 $\mu$Ci/well of $^3$H-thymidine 24 hours prior to cell harvest. The thymocytes were harvested onto glass fiber filters and dried. The amount of $^3$H-thymidine incorporation was determined by liquid scintillation counting method.

The results obtained indicated that TGF-$\beta$2 inhibited incorporation of $^3$H-thymidine into the DNA of murine thymocytes with an ED$_{50}$ of approximately 4 pM. The TGF-$\beta$2$_{16-47}$ dimer was also active as an inhibitor of thymocyte proliferation in this assay with an ED$_{50}$ of 57 nM. However, both TGF-$\beta$1$_{16-31}$ dimer and TGF-$\beta$2$_{16-31}$ dimer did not affect $^3$H-thymidine incorporation at concentrations up to 0.8 $\mu$M.

EXAMPLE 4

TGF-$\beta$ receptor binding assay

Rat muscle myoblasts (L6, American Type Culture Collection) were plated in 6-well culture plates and cultured in DMEM supplemented with 100 units/ml penicillin, 100 $\mu$g/ml streptomycin, 2 mM L-glutamine, 10% FBS until the cells were 70-90% confluent. Medium was aspirated from the wells; and 1 ml of ice cold 20 mM glycine, 135 mM NaCl, pH 3.0 was added to each well for 2 min. The buffer was aspirated and each well was rinsed 2 times with 1 ml of DMEM, 25 mM Hepes, pH 7.4, 0.1% BSA. Samples of TGF-$\beta$1 and TGF-$\beta$2 (3 to 1600 pM) and of peptides (0.1 to 30 $\mu$M), each containing 25 pM $^{125}$I-TGF-$\beta$1 or $^{125}$I-TGF-$\beta$2 were prepared in DMEM, 25 mM Hepes, pH 7.4, 0.1% BSA and added in 500 $\mu$l aliquots to the wells. Radiolabeled TGF-$\beta$ samples (500 $\mu$l) either without unlabeled TGF-$\beta$ or with excess unlabeled TGF-$\beta$ (20-25 nM) were prepared and added to other wells. After 1 hr incubation at room temperature, each well was rinsed 2 times with 1 ml of Hank's balanced saline solution, 0.1% BSA. To each well, 500 $\mu$l of 1% Triton X-100, 10% glycerol, 20 mM Hepes, pH 7.4, 0.01% BSA was added and incubated at 37° C. with rotation for 30 min to lyse the cells. Samples were transferred into gamma-counting vials and counted for 1 min each. The results are presented in Table 2.

TABLE 2

Ability of the peptides to compete against binding of $^{125}$I-TGF-$\beta$ to L6 rat muscle myoblasts

| Peptide | | $^{125}$I-TGF-$\beta$ | ED$_{50}$ |
|---|---|---|---|
| TGF-$\beta$1 | | TGF-$\beta$1 | 10-30 pM |
| TGF-$\beta$2 | | TGF-$\beta$2 | 100-130 pM |
| TGF-$\beta$1$_{16-31}$ | dimer | TGF-$\beta$1, TGF-$\beta$2 | 10-15 $\mu$M |
| | monomer | TGF-$\beta$1, TGF-$\beta$2 | not active |
| TGF-$\beta$1$_{16-47}$ | dimer | TGF-$\beta$1 | not active |
| | monomer | TGF-$\beta$1 | not active |
| TGF-$\beta$2$_{16-31}$ | dimer | TGF-$\beta$2 | 30 $\mu$M |
| | monomer | TGF-$\beta$2 | not active |
| TGF-$\beta$2$_{16-47}$ | dimer | TGF-$\beta$2 | 3 $\mu$M |
| | monomer | TGF-$\beta$2 | 30 $\mu$M |

The results obtained indicate that TGF-$\beta$1 competed against binding of $^{125}$I-TGF-$\beta$1, and TGF-$\beta$2 competed against binding of $^{125}$I-TGF-$\beta$2 for L6 rat muscle myoblasts, as previously reported by Segarini et al., J. Biol. Chem., 262:14655-14662 (1987). From the competitive binding data, the apparent dissociation constants were estimated to be 10-30 pM for TGF-$\beta$1 and 100-130 pM for TGF-$\beta$2. TGF-$\beta$1$_{16-31}$ and TGF-$\beta$2$_{16-47}$ peptide monomers, and TGF-$\beta$1$_{16-47}$ and TGF-$\beta$2$_{16-31}$ peptide monomers and dimers at concentrations of up to 30 $\mu$M were found to be either inactive or weakly active in competing against the binding of $^{125}$I-TGF-$\beta$1 or $^{125}$I-TGF-$\beta$2. However, TGF-$\beta$2$_{16-47}$ dimer competed against the binding of $^{125}$I-TGF-$\beta$2 with an apparent dissociation constant of approximately 3 $\mu$M. TGF-$\beta$1$_{16-31}$ peptide dimer competed against the binding of $^{125}$I-TGF-$\beta$1 with an apparent dissociation constant of 10-15 $\mu$M.

EXAMPLE 5

Localization of TGF-$\beta$2$_{16-47}$ peptide activity and the disulfide bonds To localize the regions of the TGF-$\beta$2$_{16-47}$ peptide responsible for biological activity, TGF-$\beta$2$_{32-47}$ was synthesized and compared to TGF-$\beta$2$_{16-31}$. TGF-$\beta$2$_{16-31}$ peptide, the N-terminal half of the TGF-$\beta$2$_{16-47}$ peptide, was found to be inactive in the mink lung epithelial cell and thymocyte proliferation assays and in the receptor binding assay, performed as discussed above. The dimeric form of the TGF-$\beta$3$_{32-47}$ peptide was prepared by forming a disulfide bond at Cys$_{44}$ between the two monomeric peptides.

TABLE 3

Competition against $^{125}$I-TGF-$\beta$2 in binding to L6 rat muscle myoblast TGF-$\beta$ receptor

| Peptide | | ED$_{50}$ |
|---|---|---|
| TGF-$\beta$2 | | 60 pM |
| TGF-$\beta$2$_{32-47}$ | dimer | not active |
| | monomer | not active |

As shown in Table 3, the TGF-$\beta$2$_{32-47}$ peptide as monomer and as dimer at concentrations up to 30 $\mu$M did not compete against the binding of $^{125}$I-TGF-$\beta$2 to the L6 rat muscle myoblasts. Furthermore, as shown in Table 4, the peptide as monomer and dimer at concentrations up to 10 $\mu$M did not inhibit the proliferation of mink lung epithelial cells. Since TGF-$\beta$2$_{16-31}$ and TGF-$\beta$2$_{32-47}$ peptides were not active in these assays, the activity of the TGF-$\beta$2$_{16-47}$ peptide resides in the full length peptide.

The TGF-$\beta$2$_{16-47}$ peptide contains two cysteine residues, Cys$_{16}$ and Cys$_{44}$. It has been demonstrated by assaying for the reduced form of cysteine, that the two monomers are linked by a single disulfide bond, rather than two disulfide bonds involving both Cys$_{16}$ and Cys$_{44}$. Dimerization could thus occur by a disulfide bond between Cys$_{16}$-Cys$_{16'}$Cys$_{44}$-Cys$_{44'}$ or Cys$_{16}$-Cys$_{44}$. Two peptides, TGF-$\beta$2$_{16-47}$Ser$_{16}$ and TGF-$\beta$2$_{16-47}$Ser$_{44'}$ in which either Cys$_{16}$ or Cys$_{44}$ had been substituted with serine respectively, were synthesized as described in Example 1. Each of these peptides was able to dimerize to like peptides only by forming Cys$_{16}$-Cys$_{16}$ or Cys$_{44}$-Cys$_{44}$ disulfide bonds. The results are shown in Table 4.

TABLE 4

Activities of TGF-$\beta$2$_{32-47}$ peptide and TGF-$\beta$2$_{16-47}$ peptides with Cys to Ser substitutions. Inhibition of proliferation of mink lung epithelial cells.

| Peptide | | ED$_{50}$ |
|---|---|---|
| TGF-$\beta$2 | | 1.6 pM |
| TGF-$\beta$2$_{32-47}$ | dimer | not active |
| | monomer | not active |
| TGF-$\beta$2$_{16-47}$Ser$_{16}$ | dimer | 380 nM |
| | monomer | 1.3 $\mu$M |
| TGF-$\beta$2$_{16-47}$Ser$_{44}$ | dimer | 450 nM |
| | monomer | not active |

The results obtained in Table 4 indicate that TGF-$\beta$2$_{16-47}$Ser$_{16}$ peptide monomer and dimer inhibited the proliferation of mink lung epithelial cells with an ED$_{50}$ of 1.3 $\mu$M and 380 nM, respectively. While TGF-$\beta$2$_{16-47}$Ser$_{44}$ peptide dimer inhibited cell proliferation with an $ED_{50}$ of 450 nM, the peptide monomer was inactive at concentrations of up to 10 µM.

Thus, these Ser-substituted peptides are significantly less active than TGF-$\beta 2_{16-47}$ peptide dimer in inhibiting proliferation of mink lung epithelial cells. These results suggest that the peptide dimer with disulfide bond between $Cys_{16}$ of one peptide and $Cys_{44}$ of the other peptide is the form that is most active in inhibiting the proliferation of mink lung epithelial cells with $ED_{50}$ in the range of 4–nM.

Thus, peptides with the biological properties of TGF-$\beta$ have been disclosed. Although the preferred embodiments of the subject invention have been described in some detail, it is understood that obvious variations can be made without departing from the spirit and the scope of the invention as defined by the appended claims.

---

We claim:

1. A peptide dimer comprising the amino acid sequence CLRPLYIDFKRDLGWKWIHEPK-

GYNANFCAGA (SEQ ID NO: 2) wherein the monomeric form of the peptide dimer is less than the full length TGF-B2 sequence.

2. A composition comprising the peptide of claim 1 and a pharmacologically acceptable carrier thereof.

3. A homodimeric peptide comprising a monomeric amino acid sequence of CLRPLYIDFKRDLGWKWIHEPKGYNANFCAGA (SEQ ID NO: 2) wherein the monomers are linked via at least one interpeptide disulfide bond between at least one set of cysteine residues.

4. A composition comprising the peptide of claim 3 and a pharmacologically acceptable carrier therefor.

5. The peptide according to claim 3 wherein the amino terminal cysteine residues are linked via a disulfide bond.

6. A composition comprising the peptide of claim 5 and a pharmacologically acceptable carrier thereof.

7. The peptide according to claim 3 wherein the carboxy terminal cysteine residues are linked via a disulfide bond.

8. A composition comprising the peptide of claim 7 and a pharmacologically acceptable carrier thereof.

9. The peptide according to claim 3 comprising the amino acid sequence

CLRPLYIDFKRDLGWKWIHEPKGYNANFCAGA (SEQ. ID NO: 2)

CLRPLYIDFKRDLGWKWIHEPKGYNANFCAGA (SEQ. ID NO: 2)

wherein the amino terminal cysteine residue of one monomer is linked to the carboxy terminal cysteine residue of the other monomer.

10. A composition comprising the peptide of claim 9 and a pharmaceutically acceptable carrier therefor.

11. A method of mimicking the effects of TGF-Bs comprising administering to a patient an effective amount of the composition of claim 2.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Cys Val Arg Gln Leu Tyr Ile Asp Phe Arg Lys Asp Leu Gly Trp Lys
1               5                   10                  15

Trp Ile His Glu Pro Lys Gly Tyr His Ala Asn Phe Cys Leu Gly Pro
            20                  25                  30
```

( 2 ) INFORMATION FOR SEQ ID NO:2:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Cys Leu Arg Pro Leu Tyr Ile Asp Phe Lys Arg Asp Leu Gly Trp Lys
1               5                   10                  15

Trp Ile His Glu Pro Lys Gly Tyr Asn Ala Asn Phe Cys Ala Gly Ala
            20                  25                  30
```

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Cys Val Arg Gln Leu Tyr Ile Asp Phe Arg Lys Asp Leu Gly Trp Lys
1               5                   10                  15
```

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Cys Leu Arg Pro Leu Tyr Ile Asp Phe Lys Arg Asp Leu Gly Trp Lys
1               5                   10                  15
```